(12) United States Patent
Matsuo et al.

(10) Patent No.: US 9,579,229 B2
(45) Date of Patent: Feb. 28, 2017

(54) HAND JOINT SUPPORTER

(71) Applicant: Kowa Company, Ltd., Aichi (JP)

(72) Inventors: Kazuhiko Matsuo, Tokyo (JP);
Hidefumi Koga, Nara (JP)

(73) Assignee: KOWA COMPANY, LTD. (JP)

( * ) Notice: Subject to any disclaimer, the term of this patent is extended or adjusted under 35 U.S.C. 154(b) by 0 days.

(21) Appl. No.: 14/628,929

(22) Filed: Feb. 23, 2015

(65) Prior Publication Data

US 2015/0164671 A1 Jun. 18, 2015

Related U.S. Application Data

(63) Continuation of application No. 13/522,612, filed as application No. PCT/JP2011/051218 on Jan. 24, 2011, now abandoned.

(30) Foreign Application Priority Data

Jan. 22, 2010 (JP) ................. 2010-012510

(51) Int. Cl.
*A61F 13/00* (2006.01)
*A61F 5/01* (2006.01)
(Continued)

(52) U.S. Cl.
CPC ............ *A61F 5/013* (2013.01); *A41D 13/088* (2013.01); *A61F 13/104* (2013.01);
(Continued)

(58) Field of Classification Search
CPC ....... A41D 13/088; A41D 13/08; A61F 5/013; A61F 13/104; A61F 13/107; A31F 13/08
(Continued)

(56) References Cited

U.S. PATENT DOCUMENTS

| | | |
|---|---|---|
| 2,403,201 A | 7/1946 | Wildt et al. |
| 2,872,800 A | 2/1959 | Davis, Jr. et al. |

(Continued)

FOREIGN PATENT DOCUMENTS

| | | |
|---|---|---|
| EP | 1621164 A1 | 2/2006 |
| JP | 6285108 A | 10/1994 |

(Continued)

OTHER PUBLICATIONS

International Search Report of International Application No. PCT/JP2011/051218 dated Apr. 26, 2011.

(Continued)

*Primary Examiner* — Kim M Lewis
(74) *Attorney, Agent, or Firm* — Duquette Law Group, LLC

(57) ABSTRACT

A hand joint supporter which can reduce the load on hand joints includes a first anchor section for tightening the wearer's forearm with a tubular knitted fabric, a second anchor section for tightening the palm and back of the wearer's hand with the fabric and a hole anchor section formed as a roughly circular through-hole in the vicinity of the second anchor section. A supporting section extends lengthwise in the fabric across the part covering the caprometacarpal joint and is joined to the first anchor section and the hole anchor section so as to support the wearer's hand joints. Stretch resistance, in the circumferential direction of the fabric of the first anchor part is larger than that of a base fabric section, and stretch resistance, in the length width direction of the fabric, of the supporting section is larger than that of the base fabric section.

9 Claims, 10 Drawing Sheets

(51) Int. Cl.
*A41D 13/08* (2006.01)
*A61F 13/10* (2006.01)
*D04B 1/18* (2006.01)

(52) U.S. Cl.
CPC .............. *A61F 13/107* (2013.01); *D04B 1/18* (2013.01); *A41D 2500/10* (2013.01); *D10B 2509/028* (2013.01)

(58) Field of Classification Search
USPC ................................ 2/16; 602/20, 21, 60–64
See application file for complete search history.

(56) References Cited

U.S. PATENT DOCUMENTS

| 2,910,852 | A | 11/1959 | Herbert et al. |
| 4,967,419 | A | 11/1990 | Elliott |
| 5,154,690 | A | 10/1992 | Shiono |
| 6,267,743 | B1* | 7/2001 | Bodenschatz ......... A61F 5/0106 602/60 |
| 7,485,111 | B1* | 2/2009 | Choi .................... A61K 9/0014 156/60 |
| 2004/0154070 | A1 | 8/2004 | Gregory |

FOREIGN PATENT DOCUMENTS

| JP | 7303726 A | 11/1995 |
| JP | 10295870 A | 11/1998 |
| JP | 3104396 U | 9/2004 |
| JP | 2005000549 A | 1/2005 |
| WO | WO 00/67600 | 11/2000 |

OTHER PUBLICATIONS

European Search Report of European Application No. 11734798.9 Dated Dec. 10, 2013.

* cited by examiner

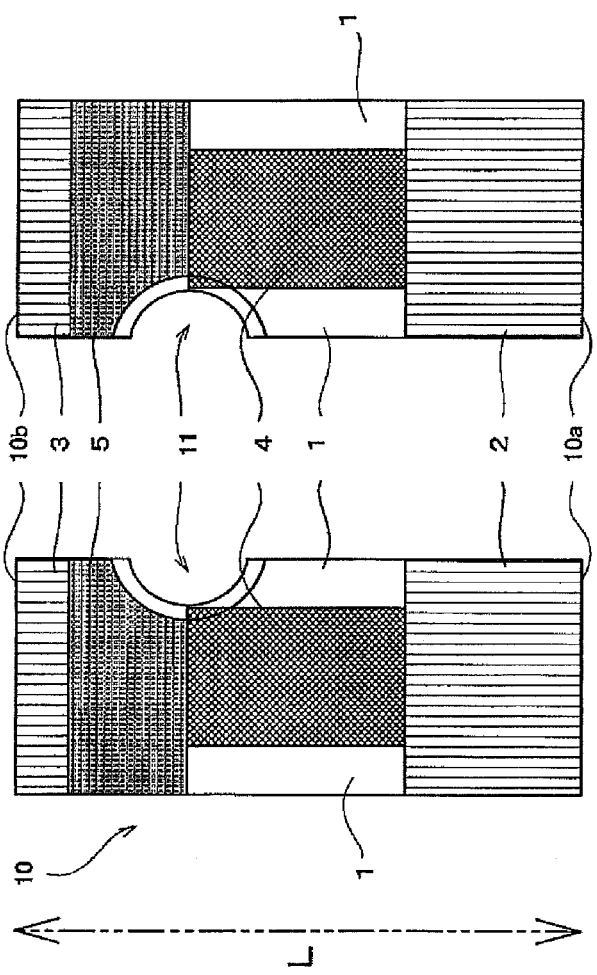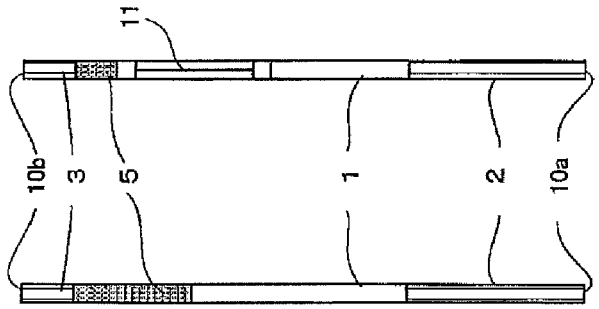

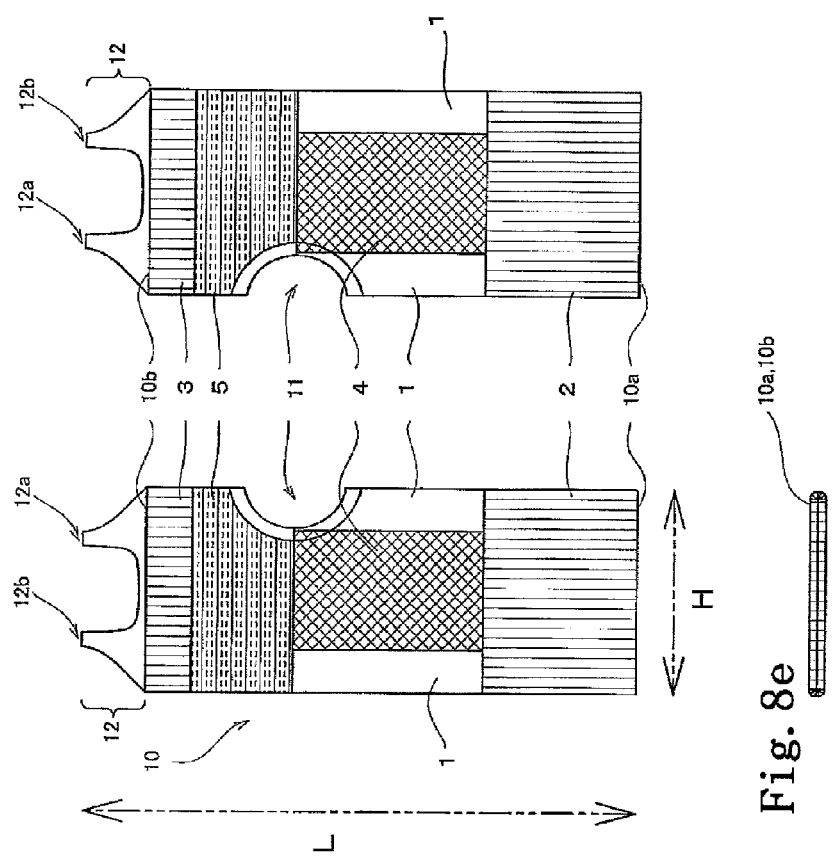

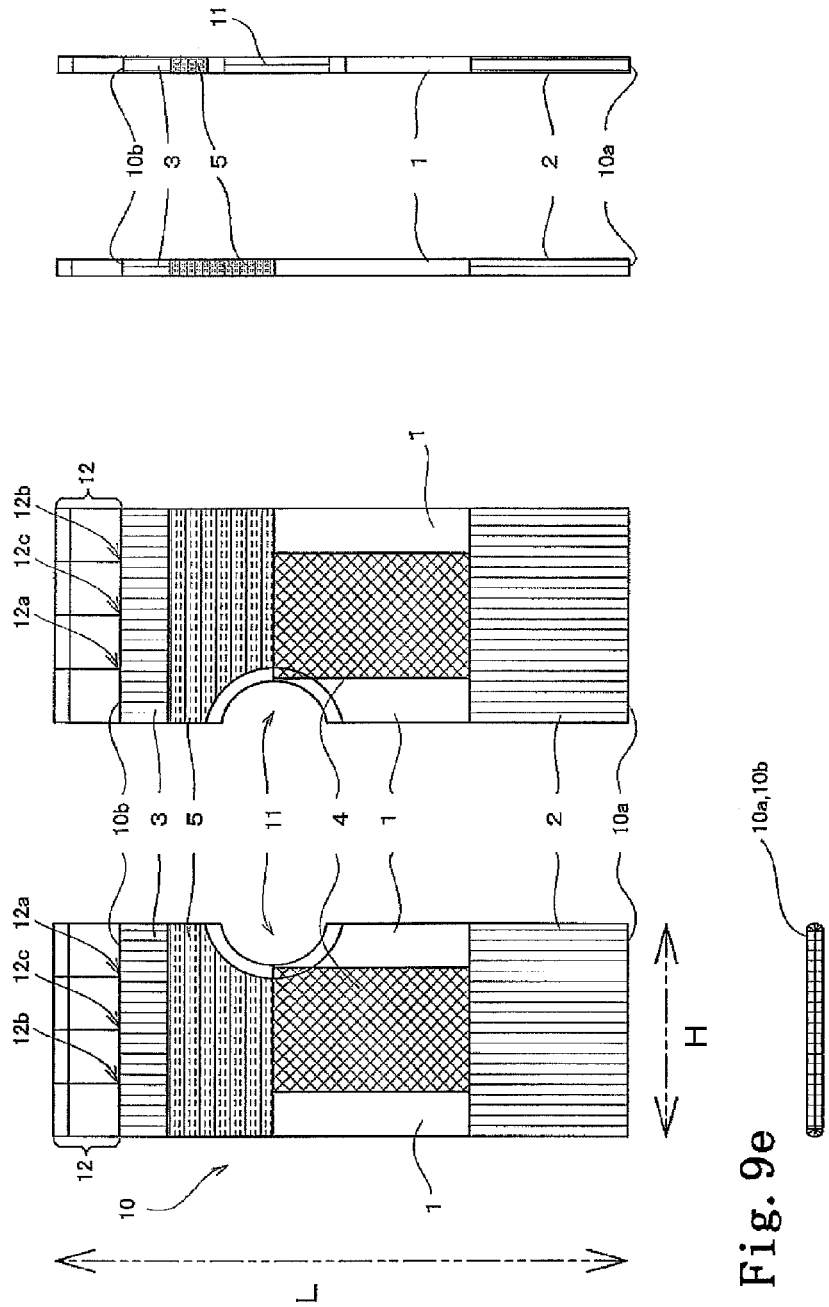

HAND JOINT SUPPORTER

PRIORITY

This application is a continuation application of U.S. Ser. No. 13/522,612 which was filed on Jul. 17, 2012 and is still pending. That application, in turn, was the entry into the national phase in the U.S. of International Application No. PCT/JP2011/051218 which was filed on Jan. 24, 2011. That application in turn claimed priority to Japanese Application No. 2010-012510 which was filed on Jan. 22, 2010.

TECHNICAL FIELD

The present invention relates to a hand joint supporter which can support wearer's daily motion, and particularly, to a hand joint supporter having a taping function of improving stability of the hand joints, thereby reducing the burden on the hand joints and also preventing an inflammation of the tendons of the hand.

BACKGROUND ART

A supporter for wrist restraint in the related art has a supporter main body which is formed in an approximately tubular shape, can expand and contract at least in the circumferential direction among the circumferential direction and the longitudinal direction, and can cover a site from the vicinity of the wrist of the forearm section to at least the vicinity of the bases of the four fingers except for the thumb, an opening portion for the thumb formed in the supporter main body, and a support which extends along the longitudinal direction on the little finger side of the supporter main body inserted into a pocket, wherein the support is provided so as to be able to extend from at least the vicinity of the wrist of the forearm section on which the support is mounted, to the side portion on the little finger side of the palm over a pisiform bone site (refer to PTL 1, for example).

CITATION LIST

Patent Literature

[PTL 1] JP-A-2005-549

SUMMARY OF INVENTION

Technical Problem

The supporter for wrist restraint in the related art is a supporter for restraining the movement of the wrist as a conservative therapy in a case where a bruise, a sprain, or an inflammation of the tendon develops in the wrist, and is not provided with a support on the thumb side and the back side of the hand and the palm side of the hand. In particular, in the supporter for wrist restraint in the related art, as the support, a support which bends when an external force or a load is added thereto is also included. However, it is regarded as being formed so that the fixed feeling is not lost by the bending, and is formed of, for example, synthetic resin, metal, carbon fiber, glass fiber, wood, or the like.

For this reason, in the supporter for wrist restraint in the related art, there is a problem in that after the approximately tubular supporter main body is formed, a process of attaching the support to the supporter main body by sewing, tack fixing, attachment, adhesion, or the like is required, so that the manufacturing process is complicated.

The present invention has been made to solve the problem as described above and has an object to provide a hand joint supporter in which the manufacturing process of disposing a support that is a separate body from a supporter main body to the supporter main body is not required, while reducing the burden on the hand joints, so that it is possible to prevent an inflammation of the tendons of the hand.

Solution to Problem

A hand joint supporter according to the invention includes: a first anchor section which is knitted to go around one end of a tubular knitted fabric and makes the tubular knitted fabric tighten on the forearm of the wearer; a second anchor section which is knitted to go around the other end of the tubular knitted fabric, surrounds portions corresponding to the second metacarpal bone, the third metacarpal bone, the fourth metacarpal bone, and the fifth metacarpal bone in the vicinity of the carpometacarpal joint in at least the third metacarpal bone of the wearer, and makes the tubular knitted fabric tighten on the palm and the back of the hand of the wearer; a hole anchor section which is formed as an approximately circular through-hole in the vicinity of the second anchor section in the tubular knitted fabric to insert the thumb of the hand of the wearer therethrough; and a supporting section which is knitted to extend in the length direction of the tubular knitted fabric over portions corresponding to the carpometacarpal joints of the wearer on the front face and/or back face side of the tubular knitted fabric and is connected to the first anchor section and the hole anchor section, thereby supporting the hand joints of the wearer, wherein the stretch resistance of the first anchor section in the circumferential direction of the tubular knitted fabric is larger than the stretch resistance of a base fabric section in the circumferential direction of the tubular knitted fabric, and the stretch resistance of the supporting section in the length direction of the tubular knitted fabric is larger than the stretch resistance of the base fabric section in the length direction of the tubular knitted fabric.

Advantageous Effects of Invention

In the hand joint supporter according to the invention, the hand joints of the wearer are stabilized by performing the inhibiting of the palmar flexion and/or the dorsal flexion of the hand joints, and a load which is applied to a tendon that is located at the hand joints is reduced, so that an inflammation of the tendons of the hand can be prevented.

BRIEF DESCRIPTION OF DRAWINGS

FIG. 1(a) is a front view showing a schematic configuration of a hand joint supporter related to the first embodiment, FIG. 1(b) is a back view of the hand joint supporter shown in FIG. 1(a), FIG. 1(c) is a left side view of the hand joint supporter shown in FIG. 1(a), FIG. 1(d) is a right side view of the hand joint supporter shown in FIG. 1(a), and FIG. 1(e) is a plan view and bottom view of the hand joint supporter shown in FIG. 1(a).

FIG. 8(a) is a front view showing the schematic configuration of a hand joint supporter related to the second embodiment, FIG. 8(b) is a back view of the hand joint supporter shown in FIG. 8(a), FIG. 8(c) is a left side view of the hand joint supporter shown in FIG. 8(a), FIG. 8(d) is a right side view of the hand joint supporter shown in FIG. 8(a), and FIG. 8(e) is a plan view and bottom view of the hand joint supporter shown in FIG. 8(a).

FIG. 9(a) is a front view showing the schematic configuration of another hand joint supporter related to the second embodiment, FIG. 9(b) is a back view of the hand joint supporter shown in FIG. 9(a), FIG. 9(c) is a left side view of the hand joint supporter shown in FIG. 9(a), FIG. 9(d) is a right side view of the hand joint supporter shown in FIG. 9(a), and FIG. 9(e) is a plan view and bottom view of the hand joint supporter shown in FIG. 9(a).

DESCRIPTION OF EMBODIMENTS

First Embodiment of the Invention

Figure 2:
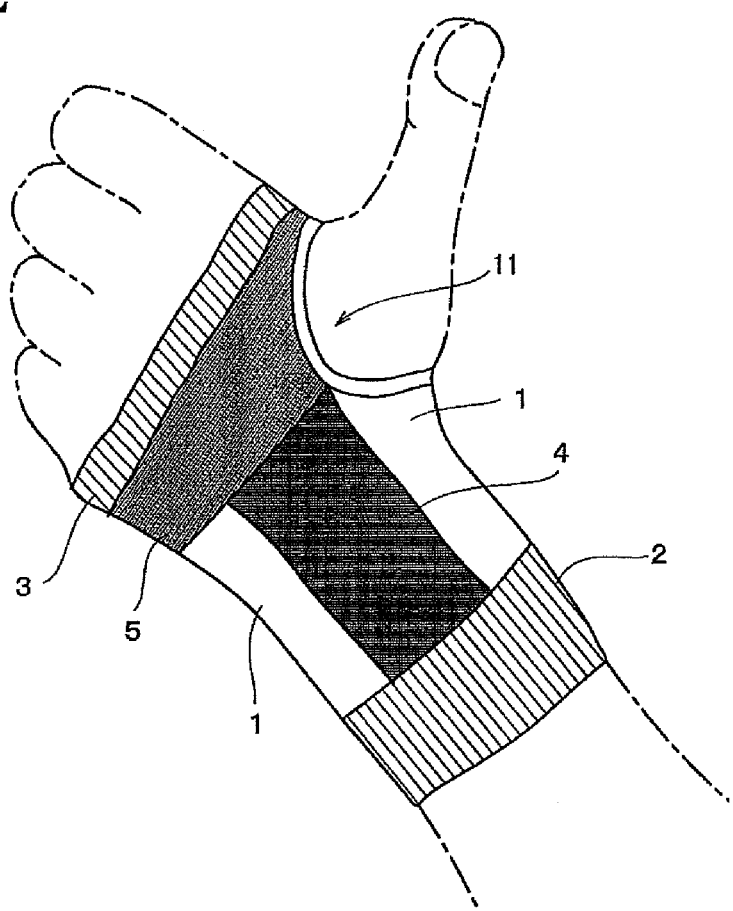
FIG. 2 is a perspective view showing a wearing state of the hand joint supporter shown in FIG. 1.

In FIGS. 1 and 2, a hand joint supporter 10 is made of a tubular knitted fabric which is knitted by circular knitting by a hosiery knitting machine (for example, a type of knitting machine (the number of needles: 256) manufactured by Lonati Co.), and is a supporter which comes into close contact with the body surface of the wearer, thereby assisting the hand joints of the wearer.

The hand joint supporter 10 has a desired function such as a taping function by performing different knitting with respect to a base fabric section 1 that is a knitted fabric which is knitted in a plain stitch, a rib stitch, a tuck stitch, a float stitch, a pile stitch, or the like by using an upper thread, an under thread, and a rubber thread as knitting yarn. In addition, the base fabric section 1 related to this embodiment is a knitted fabric which is knitted in a tuck stitch (hereinafter referred to as a tuck stitch knitted fabric).

Here, the tuck stitch knitted fabric is a knitted fabric in which a certain loop is not made temporarily when knitting the fabric and loops are made together when knitting the next course. In addition, in this embodiment, in consideration of a balance with density, the number of tucks is set to be twice. However, the number is not limited thereto.

The hand joint supporter 10 has a first anchor section 2 which is knitted to go around one end (an upper end 10a) of the tubular knitted fabric and makes the hand joint supporter 10 tighten on the forearm of a wearer.

The first anchor section 2 is knitted such that the stretch resistance thereof in the circumferential direction H of the hand joint supporter 10 (the tubular knitted fabric) is larger than the stretch resistance of the base fabric section 1 in the circumferential direction H of the hand joint supporter 10. That is, when tension in a case where a certain elongation has been imparted to a material from a state where elongation is not imparted is set to be F, the tension of the base fabric section 1 in the circumferential direction H of the hand joint supporter 10 is set to be $F_{H1}$, and the tension of the first anchor section 2 in the circumferential direction H of the hand joint supporter 10 is set to be $F_{H2}$, the first anchor section 2 has such a magnitude relationship of $F_{H2} > F_{H1}$ that it has a strong tightening force in the circumferential direction H of the hand joint supporter 10, compared to the base fabric section 1.

Specifically, by making the first anchor section 2 be a knitted fabric knitted in a moss stitch (hereinafter referred to as a moss stitch knitted fabric), it is possible to make the stretch resistance thereof in the circumferential direction H of the hand joint supporter 10 large with respect to the base fabric section 1 that is the tuck stitch knitted fabric.

In addition, the moss stitch knitted fabric is a knitted fabric in which a plain stitch and a tuck (a structure in which no loop protrudes over a given course and a plurality of loops protrude over the subsequent course) appear alternately or every few courses in the course direction and the wale direction. For this reason, in the first anchor section 2, the plain stitch and the tuck are used in combination, whereby it is possible to make protuberances or openwork stitches on the surface of a knitted fabric and a mesh pattern, such as a moss, appears.

In this manner, the first anchor section 2 is knitted to surround the forearm of a wearer, and the stretch resistance of the first anchor section 2 in the circumferential direction H of the hand joint supporter 10 is larger than the stretch resistance of the base fabric section 1 in the circumferential direction H of the hand joint supporter 10, whereby it is possible to fix the hand joint supporter 10 to the forearm of a wearer and suppress slipping-off of the upper end 10a of the hand joint supporter 10 during palmar flexion of the hand joints. Further, the first anchor section 2 is connected to a supporting section 4 (described later), thereby also functioning as an anchor of the supporting section 4.

Figure 3A:
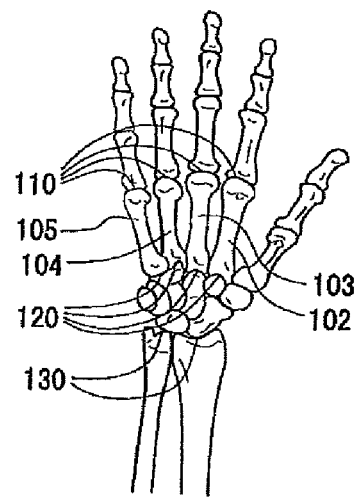
FIG. 3(a) is an explanatory diagram for describing the joints and the bones of the hand.

Further, the hand joint supporter 10 has a second anchor section 3 which is knitted to go around the other end (a lower end 10b) of the tubular knitted fabric, surrounds portions corresponding to a second metacarpal bone 102, a third metacarpal bone 103, a fourth metacarpal bone 104, and a fifth metacarpal bone 105 in the vicinity of metacarpophalangeal joints 110 of a wearer, and makes the hand joint supporter 10 tighten on the palm and the back of the hand of the wearer, as shown in FIG. 3(a).

The second anchor section 3 is knitted such that the stretch resistance thereof in the circumferential direction H of the hand joint supporter 10 is larger than the stretch resistance of a buffer section 5 (described later) in the circumferential direction H of the hand joint supporter 10. That is, when the tension of the second anchor section 3 in the circumferential direction H of the hand joint supporter 10 is set to be $F_{H3}$ and the tension of the buffer section 5 in the circumferential direction H of the hand joint supporter 10 is set to be $F_{H5}$, the second anchor section 3 has such a magnitude relationship of $F_{H3}>F_{H5}$ that it has a strong tightening force in the circumferential direction H of the hand joint supporter 10, compared to the buffer section 5.

Specifically, by making the second anchor section 3 be a moss stitch knitted fabric, it is possible to make the stretch resistance thereof in the circumferential direction H of the hand joint supporter 10 large with respect to the buffer section 5 that is a mesh stitch knitted fabric which will be described later.

In this manner, the second anchor section 3 is knitted to surround the palm and the back of the hand of a wearer and the stretch resistance of the second anchor section 3 in the circumferential direction H of the hand joint supporter 10 is larger than the stretch resistance of the buffer section 5 in the circumferential direction H of the hand joint supporter 10, whereby it is possible to fix the hand joint supporter 10 to the palm and the back of the hand of a wearer and suppress slipping-off of the lower end 10b of the hand joint supporter 10 during palmar flexion of the hand joints.

In addition, if a tightening force on the palm and the back of the hand of a wearer by the second anchor section 3 is too strong, the gaps between the fingers (the second finger (the index finger or the forefinger), the third finger (the middle finger), the fourth finger (the ring finger), and the fifth finger (the little finger)) of the hand of a wearer cannot be fully opened, thereby causing interference with work such as keyboard operation of a personal computer.

For this reason, the hand joint supporter 10 related to this embodiment is made such that the density of the second anchor section 3 is adjusted (for example, to make a tightening force thereof about 10% smaller with respect to the first anchor section 2), whereby the movement of the fingers of the hand with the hand joint supporter 10 worn thereon is not prevented. That is, it is preferable that the hand joint supporter 10 related to this embodiment have a magnitude relationship of $F_{H2}>F_{H1}>F_{H3}>F_{H5}$ so as to have a moderate tightening force in the circumferential direction H of the hand joint supporter 10.

A hole anchor section 11 is formed as an approximately circular through-hole in the vicinity of the second anchor section 3 in the hand joint supporter 10 to insert the first finger (the thumb or the big finger) of the hand of a wearer therethrough.

In addition, the hole anchor section 11 related to this embodiment is made by making a cut in the tubular knitted fabric which becomes the hand joint supporter 10, folding a cut edge back to the inside of the tubular knitted fabric, and sewing it using a sewing machine. However, the hole anchor section 11 may also be formed by knitting without cutting out the tubular knitted fabric. In particular, it is preferable that a sewn section constituting the hole anchor section 11 be formed as a flexible bellows by using a sewing thread having high stretch property and increasing the number of stitches per inch of the sewing machine, to reduce a pressing force which is imparted on the thumb of a wearer.

The hole anchor section 11 positions the hand joint supporter 10 with respect to the hand joints of the wearer by inserting the thumb of the hand of the wearer therethrough and also suppresses the rotational movement in the circumferential direction H or the parallel displacement in the length direction L of the hand joint supporter 10, thereby being able to prevent a position shift. Further, the hole anchor section 11 is connected to the supporting section 4 (described later), thereby also functioning as an anchor of the supporting section 4.

The supporting section 4 is knitted to extend in the length direction L of the hand joint supporter 10 over portions corresponding to carpometacarpal joints 120 of a wearer on the front face and/or back face side of the hand joint supporter 10 and is connected to the first anchor section 2 and the hole anchor section 11, thereby supporting the hand joints of the wearer. That is, the supporting section 4 is locked at the first anchor section 2 on the forearm side of a wearer and locked at the hole anchor section 11 on the hand side of the wearer.

In addition, the supporting section 4 related to this embodiment is knitted in an approximately rectangular shape. However, as long as it extends in the length direction L of the hand joint supporter 10 over the portions corresponding to the carpometacarpal joints 120 of the wearer, the shape thereof is not limited thereto.

Further, the supporting section 4 is knitted such that the stretch resistance thereof in the length direction L of the hand joint supporter 10 is larger than the stretch resistance of the base fabric section 1 in the length direction L of the hand joint supporter 10. That is, when the tension of the base fabric section 1 in the length direction L of the hand joint supporter 10 is set to be $F_{L1}$ and the tension of the supporting section 4 in the length direction L of the hand joint supporter 10 is set to be $F_{L4}$, the supporting section 4 has such a magnitude relationship of $F_{L4}>F_{L1}$ that it has a strong tightening force in the length direction L of the hand joint supporter 10, compared to the base fabric section 1.

Specifically, by making the supporting section 4 be a knitted fabric in which a tuck stitch and a plating stitch are used in combination (hereinafter referred to as a tuck stitch-plating stitch knitted fabric), it is possible to make the stretch resistance in the length direction L of the hand joint supporter 10 large with respect to the base fabric section 1 that is a tuck stitch knitted fabric.

In addition, in the tuck stitch-plating stitch knitted fabric, expansion and contraction of the supporting section 4 in the length direction L of the hand joint supporter 10 is moderately suppressed by additionally feeding another knitting yarn (for example, woolly nylon yarn) in addition to the ground knitting yarn of the tuck stitch, and another knitting yarn is cut at the boundary between the supporting section 4 and the base fabric section 1 (a cut boss).

In this manner, the supporting section 4 is knitted to extend in the length direction L of the hand joint supporter 10 over the portions corresponding to carpometacarpal joints 120 of the wearer on the front face and/or back face side of the hand joint supporter 10, and the stretch resistance in the length direction L of the hand joint supporter 10 is larger than the stretch resistance of the base fabric section 1 in the length direction L of the hand joint supporter 10. In this way, the supporting section 4 limits the palmar flexion and/or the dorsal flexion of the hand joints of a wearer, thereby being able to secure stability of the hand joints and also reduce the load that is applied to a tendon which is located at the hand joints.

In particular, in a case where the hand joint supporter 10 is not worn, if a pain is present in the hand joints, a burden is also applied to the elbow joint or the like which compensates for an overload on the hand joints, so that there is a fear that a secondary pain may be induced. For this reason, in a person for whom the frequency of using the fingers or the hand joints is high and pain is present in the elbow or the front of the shoulder joint, pains of the elbow and the shoulder joint, which result through a chain reaction from a pain of the hand joints, can be reduced by wearing the hand joint supporter 10.

In addition, the supporting section 4 is disposed on the front face (the palm of the hand) side of the hand joint supporter 10, thereby limiting the dorsal flexion of the hand joints of the wearer, and is disposed on the back face (the back of the hand) side of the hand joint supporter 10, thereby limiting the palmar flexion of the hand joint of the wearer. For this reason, depending on pain of the hand joints of the wearer, in the case of wanting to limit the dorsal flexion of the hand joints, the hand joint supporter 10 in which the supporting section 4 is disposed only on the front face (the palm of the hand) side is also acceptable, and in the case of wanting to limit the palmar flexion of the hand joints, the hand joint supporter 10 in which the supporting section 4 is disposed only on the back face (the back of the hand) side is also acceptable.

In particular, it is preferable to dispose the supporting sections 4 on the front face and back face sides of the hand joint supporter 10, because the front face and the back face of the hand joint supporter 10 become symmetrical, so that the hand joint supporter 10 can double as left-hand and right-hand supporters.

Figure 3B:
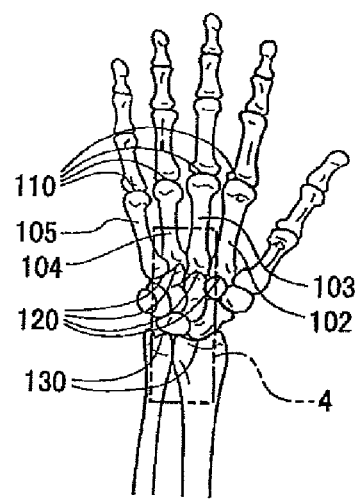
FIG. 3(b) is an explanatory diagram for describing the position of a supporting section with respect to the hand of a wearer.
Figure 3C:
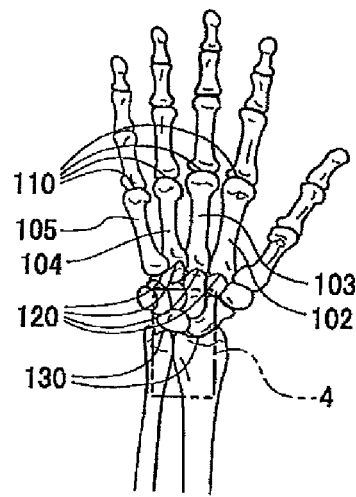
FIG. 3(c) is an explanatory diagram for describing another position of the supporting section with respect to the hand of the wearer.

Further, in a case where the supporting section 4 along with the base fabric section 1 which is knitted between the supporting sections 4 that are on the front face and back face sides of the tubular knitted fabric extends only from the vicinity (the first anchor section 2) of radiocarpal joints 130 to the vicinity of the carpometacarpal joints 120, as shown in FIG. 3(c), a holding feeling of the wrist cannot be obtained and the above-described operation and effects by the supporting section 4 cannot be obtained.

Figure 3D:
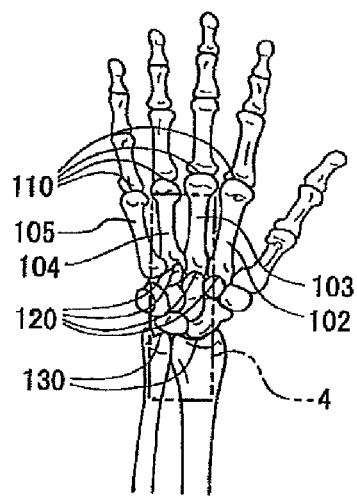
FIG. 3(d) is an explanatory diagram for describing still another position of the supporting section with respect to the hand of the wearer.

In contrast to this, in a case where the supporting section 4 and the base fabric section 1 extend from the vicinity (the first anchor section 2) of the radiocarpal joints 130 to the vicinity (the second anchor section 3) of the metacarpophalangeal joints 110, as shown in FIG. 3(d), as well as being unable to fully open the gaps between the fingers of a wearer, the palm and the back of the hand of a wearer are tightened, thereby being accompanied by a pain.

Therefore, it is preferable that the supporting section 4 and the base fabric section 1 extend from the vicinity (the first anchor section 2) of the radiocarpal joints 130 to the metacarpal bone bodies (the approximate middles of the second metacarpal bone 102, the third metacarpal bone 103, the fourth metacarpal bone 104, and the fifth metacarpal bone 105), as shown in FIG. 3(b).

In addition, in the movement of the hand joints, in addition to the palmar flexion and the dorsal flexion, radial flexion and ulnar flexion are included, and the radial flexion and the ulnar flexion are motions which are frequently used in daily life, and according to the motion, the frequency of occurrence of De Quervain syndrome that is an inflammation of the tendons extending toward the thumb from the hand is high. In contrast to this, the supporting section 4 and the base fabric section 1 limit the radial flexion and the ulnar flexion of the hand joints of a wearer, whereby prevention and improvement of De Quervain syndrome can be expected.

The buffer section 5 is a knitted fabric surrounded by the second anchor section 3, the hole anchor section 11, the supporting section 4, and the base fabric section 1 in the hand joint supporter 10 and is a knitted fabric making flexibility be provided between the second anchor section 3 and the supporting section 4.

The buffer section 5 is knitted such that the stretch resistance thereof in the length direction L of the hand joint supporter 10 is smaller than the stretch resistance of the base fabric section 1 in the length direction L of the hand joint supporter 10. That is, when the tension of the buffer section 5 in the length direction L of the hand joint supporter 10 is set to be $F_{L5}$, the buffer section 5 has such a magnitude relationship of $F_{L1} > F_{L5}$ that it has a weak tightening force in the length direction L of the hand joint supporter 10, compared to the base fabric section 1.

Specifically, by making the buffer section 5 be a knitted fabric knitted in a mesh stitch that is a knitting structure having good air permeability (hereinafter referred to as a mesh stitch knitted fabric), it is possible to make the stretch resistance in the length direction L of the hand joint supporter 10 small with respect to the base fabric section 1 that is a tuck stitch knitted fabric.

In addition, the mesh stitch knitted fabric is a knitted fabric in which a certain loop is not made temporarily when knitting the fabric and loops are made together when knitting the next course and which stretches well by being knit in the form of a mesh.

In this manner, in the buffer section 5, the stretch resistance thereof in the length direction L of the hand joint supporter 10 is smaller than the stretch resistance of the base fabric section 1 in the length direction L of the hand joint supporter 10, whereby the buffer section 5 does not tighten the palm and the back of the hand of the wearer, thereby preventing constriction of blood flow as well as allowing the gaps between the fingers of a wearer to be fully open, so that a feeling of discomfort is not caused to the wearer.

In addition, in the hand joint supporter 10 related to this embodiment, due to the knitted fabric of each site described above, the stretch resistance of the base fabric section 1 in the length direction L of the hand joint supporter 10 is larger than the stretch resistance of the first anchor section 2 in the length direction L of the hand joint supporter 10. Further, the stretch resistance of the first anchor section 2 in the length direction L of the hand joint supporter 10 is larger than the stretch resistance of the second anchor section 3 in the length direction L of the hand joint supporter 10. Further, the stretch resistance of the second anchor section 3 in the length direction L of the hand joint supporter 10 is larger than the stretch resistance of the buffer section 5 in the length direction L of the hand joint supporter 10. Further, the stretch resistance of the supporting section 4 in the circumferential direction H of the hand joint supporter 10 is approximately equal to the stretch resistance of the base fabric section 1 in the circumferential direction H of the hand joint supporter 10.

Therefore, the hand joint supporter 10 related to this embodiment satisfies a magnitude relationship shown by the following expression (1) in the tension F in the length direction L of the hand joint supporter 10. However, in the following expression (1), $F_{L2}$ is the tension of the first anchor section 2 in the length direction L of the hand joint supporter 10, and $F_{L3}$ is the tension of the second anchor section 3 in the length direction L of the hand joint supporter 10.

[Expression 1]

$$F_{L4} > F_{L1} > F_{L2} > F_{L3} > F_{L5} \qquad (1)$$

Further, the hand joint supporter 10 related to this embodiment satisfies a magnitude relationship shown by the following expression (2) in the tension F in the circumferential direction H of the hand joint supporter 10. However, in the following expression (2), $F_{H4}$ is the tension of the supporting section 4 in the circumferential direction H of the hand joint supporter 10.

[Expression 2]

$$F_{H2} > F_{H1} \approx F_{H4} > F_{H3} > F_{H5} \quad (2)$$

In addition, in this embodiment, as ground knitting yarn which is used in the moss stitch, the tuck stitch, and the mesh stitch, an upper thread which is nylon yarn having a thickness of 70 deniers and is composed of two pieces of knitting yarn, an under thread which is nylon yarn having a thickness of 30 deniers and is composed of two pieces of knitting yarn, and a rubber thread which is covering yarn (DCY: double covered yarn) in which two pieces of nylon winding yarn each having a thickness of 40 deniers are wound around a polyurethane core yarn having a thickness of 260 deniers are used. However, the threads are not limited to these materials.

For example, as the upper thread, it is preferable to select a natural fiber such as cotton, wool (cashmere, lamb, Angora, or the like), silk, or hemp, a chemical fiber such as acrylic, a material having a sweat absorbing, quick-drying, or body temperature adjusting function, or the like according to the cost of the hand joint supporter 10 or the needs of a wearer. Further, as the under thread, it is preferable to select an ester, FTY (filament twisted yarn), or an antibacterial, deodorant, or odor eliminating material according to the cost of the hand joint supporter 10 or the needs of a wearer.

Further, the woolly nylon yarn (pattern yarn) in the tuck stitch-plating stitch knitted fabric (the supporting section 4) is composed of two pieces of knitting yarn each having a thickness of 100 deniers.

Figure 4:
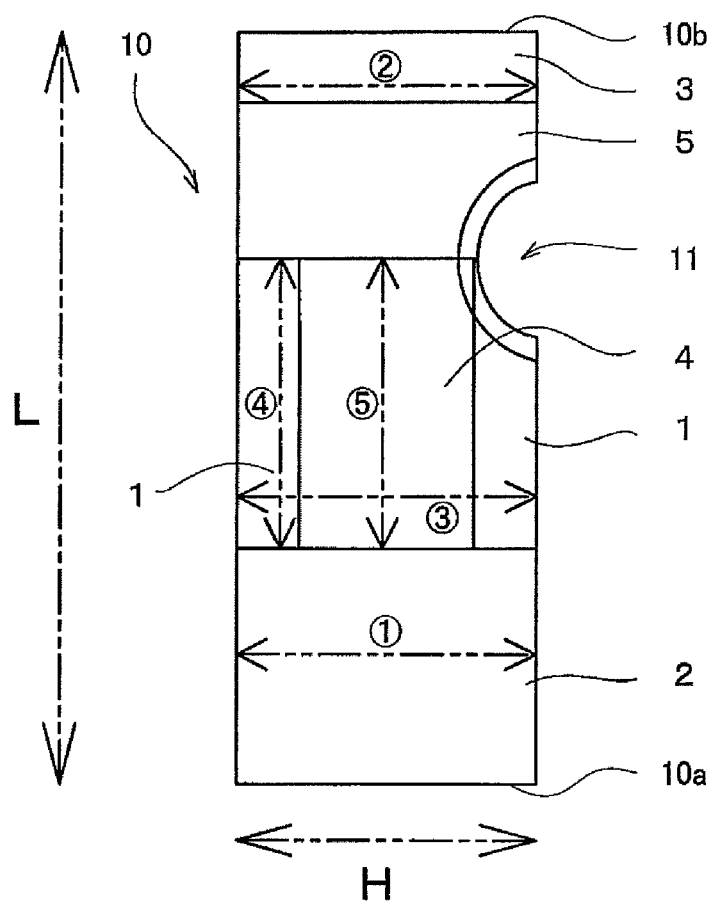
FIG. 4 is an explanatory diagram for describing sites for measuring elongation rates in the hand joint supporter shown in FIG. 1(a).

Here, the results of measurement of elongation rates (the percentage of the difference between the length when elongated (an elongated dimension) and the original length (the original dimension) to the original length) measured with respect to the respective sites (refer to FIG. 4) of the hand joint supporter 10 made according to the above-described knitting yarn and knitted fabrics by using a stretch tester (tensile load: 4 kg) are shown in Table 1 below.

TABLE 1

| | Measured site | Original dimension [cm] | Elongated dimension [cm] | Elongation rate [%] |
|---|---|---|---|---|
| Circled number 1 | Circumferential direction H of the first anchor section 2 | 8.5 | 22.0 | 158.8 |
| Circled number 2 | Circumferential direction H of the second anchor section 3 | 9.7 | 28.0 | 188.7 |
| Circled number 3 | Circumferential direction H over the base fabric section 1 and the supporting section 4 | 9.0 | 24.0 | 166.7 |
| Circled number 4 | Length direction L of the base fabric section 1 | 7.2 | 10.0 | 38.9 |
| Circled number 5 | Length direction L of the supporting section 4 | 7.2 | 9.0 | 25.0 |

TABLE 1-continued

| | Measured site | Original dimension [cm] | Elongated dimension [cm] | Elongation rate [%] |
|---|---|---|---|---|
| number 5 | direction L of the supporting section 4 | | | |

In addition, since the elongation rates in Table 1 represents the fact that the larger the value, the more easily the knitted fabric is elongated and the tension F in the above-described expressions (1) and (2) represents the fact that the larger the value, the more difficult it is for the knitted fabric to be elongated (the larger the tightening force), an inequality sign showing the magnitude relationship of the elongation rates and an inequality sign showing the magnitude relationship of the tension F become opposite to each other.

Next, the result of verification of the operation and effects of the hand joint supporter 10 related to this embodiment will be described.

Figure 5A:
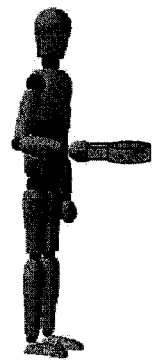
FIG. 5(a) is an explanatory diagram for describing an experimental motion.

In the first experiment, in a case where the hand joint supporter 10 is worn on the right wrist (hereinafter referred to as the time of wear) of a test subject (a 26-years-old healthy male, no anamnesis in any of the four limbs) and a case where the hand joint supporter 10 is not worn (hereinafter referred to as the time of non-wear), a state where the test subject holds in the right hand a frying pan weighing 300 g with a 1 kg weight placed therein, and the brachium and the forearm of the right arm are approximately perpendicular to each other was maintained for 30 seconds (FIG. 5(a)).

At this time, in the experiment, the myogenic potentials of the biceps brachii muscle (the muscle which bends the elbow) and the flexor carpi ulnaris muscle and the flexor carpi radialis muscle (the muscles which bend the wrist) for the final 5 seconds were measured by a surface electromyogram (FIG. 5). In addition, "MyoResearch" manufactured by Noraxon, Inc. was used in the measurement of the surface electromyogram.

Figure 5B:
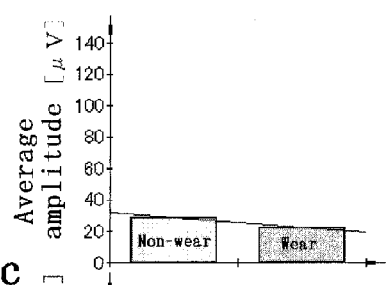
FIG. 5(b) is graphs showing the verification results by a surface electromyogram of the flexor carpi ulnaris muscle in the hand joint supporter shown in FIG. 1.
Figure 5C:
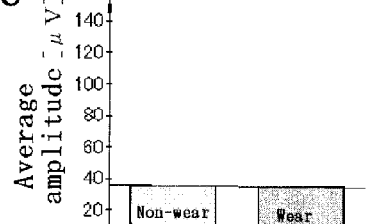
FIG. 5(c) is graphs showing the verification results by a surface electromyogram of the flexor carpi radialis muscle in the hand joint supporter shown in FIG. 1.

As shown in FIGS. 5(b) and 5(c), it can be seen that in the case of the time of wear, compared to the case of the time of non-wear, since the myogenic potentials (the average amplitudes and the muscle integrated values) of the flexor carpi ulnaris muscle and the flexor carpi radialis muscle are lowered, loads on the flexor carpi ulnaris muscle and the flexor carpi radialis muscle are reduced, so that the burden on the hand joints is reduced. In particular, the hand joint supporter 10 reduces the burden on the hand joints, thereby being able to prevent an inflammation of the tendonds of the hand.

Figure 5D:
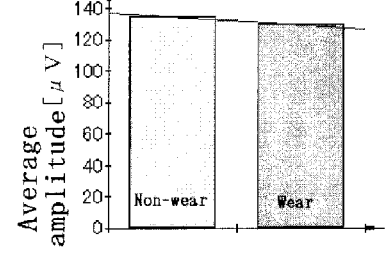
FIG. 5(d) is graphs showing the verification results by a surface electromyogram of the biceps brachii muscle in the hand joint supporter shown in FIG. 1.

Further, as shown in FIG. 5(d), it can be seen that in the case of the time of wear, compared to the case of the time of non-wear, since the myogenic potential (the average amplitude and the muscle integrated value) of the biceps brachii muscle is lowered, a load on the biceps brachii muscle is reduced, so that the burden on the hand joints is reduced.

In the second experiment, in a case where the hand joint supporters 10 are worn on the right wrists of three test subjects (healthy adult males, average age: 29±3.6-years-old, average height: 169.7±4.9 cm, and average weight: 64.3±11.9 kg) (the time of wear) and a case where the hand joint supporter 10 is not worn (the time of non-wear), the hand joints of the test subjects were palmar-flexed and dorsal-flexed in a state where the brachium of the right arm of each test subject is approximately vertical and the forearm of the right arm of each test subject is approximately horizontal. In the experiment, the amount of work of a hand joint palmar flexion moment of each test subject was measured (FIG. 6), and the amount of work of a hand joint dorsal flexion moment of each test subject was measured (FIG. 7).

Figure 6A:
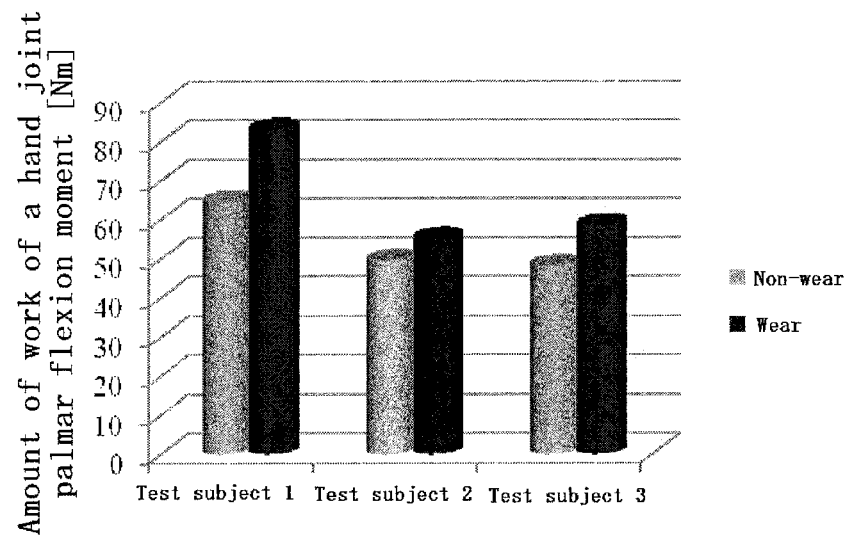
FIG. 6(a) is a graph showing the measurement results of the amount of work of a hand joint palmar flexion moment with respect to each test subject for verifying the operation and effects of the hand joint supporter shown in FIG. 1.
Figure 6B:
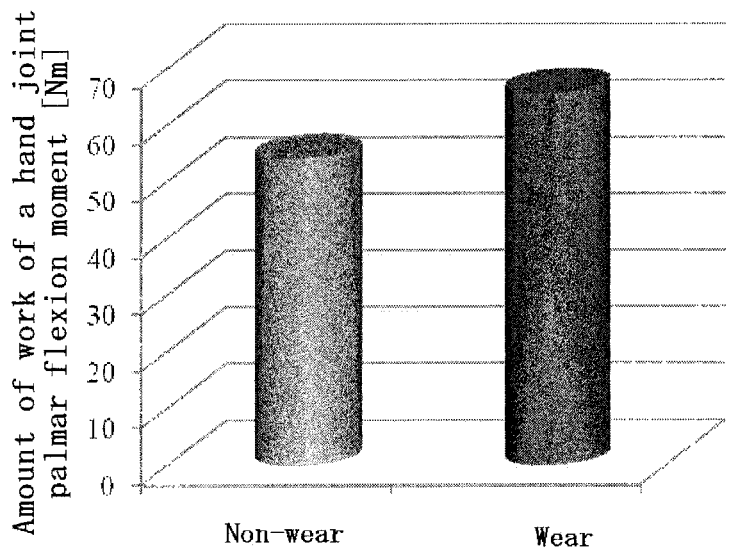
FIG. 6(b) is a graph showing the average value of the measurement results shown in FIG. 6(a).
Figure 7A:
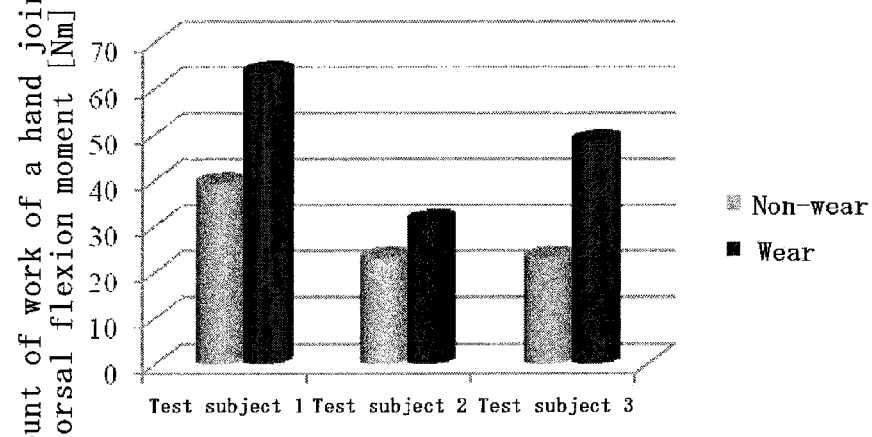
FIG. 7(a) is a graph showing the measurement results of the amount of work of a hand joint dorsal flexion moment with respect to each test subject for verifying the operation and effects of the hand joint supporter shown in FIG. 1.
Figure 7B:
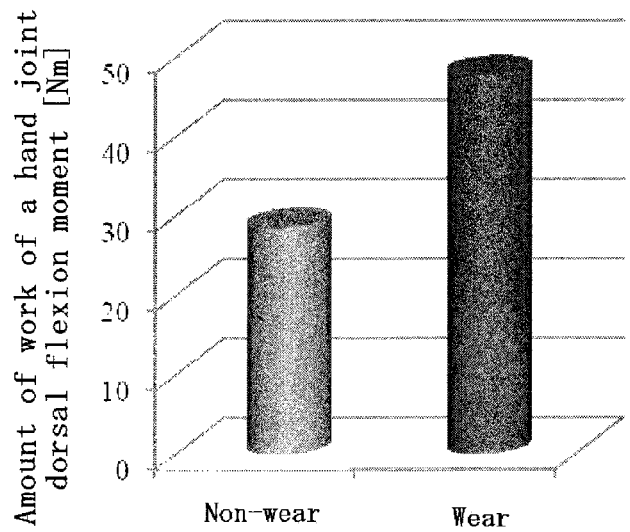
FIG. 7(b) is a graph showing the average value of the measurement results shown in FIG. 7(a).

As shown in FIGS. 6 and 7, it can be found that in all the test subjects, at the time when the hand joint supporter 10 is worn, the amount of work of a hand joint palmar flexion moment and the amount of work of a hand joint dorsal flexion moment become large compared to the time of non-wear.

Second Embodiment of the Invention

Figure 10A:
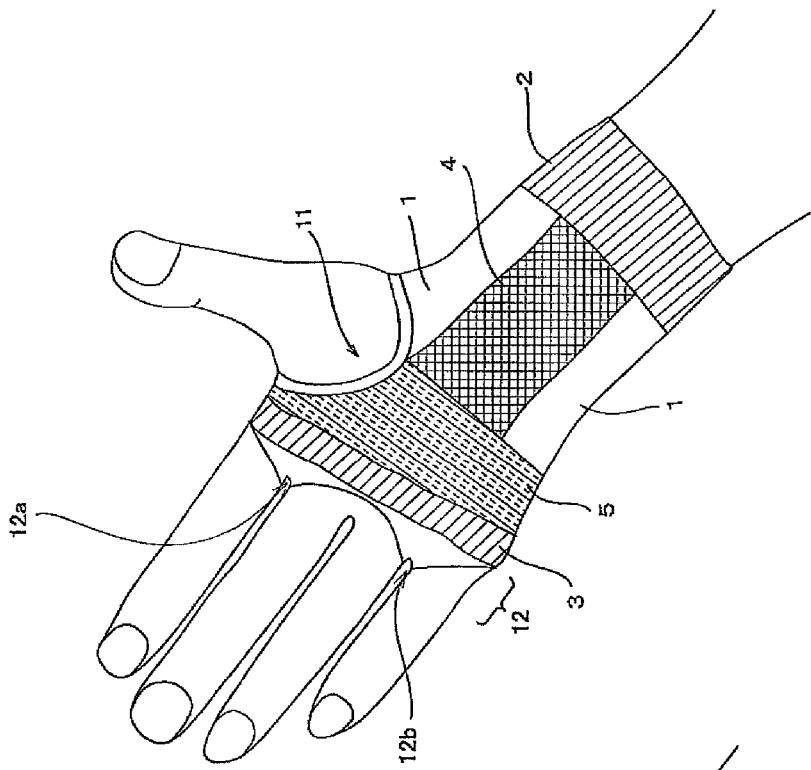
FIG. 10(a) is a perspective view showing a wearing state of the hand joint supporter shown in FIG. 8.
Figure 10B:
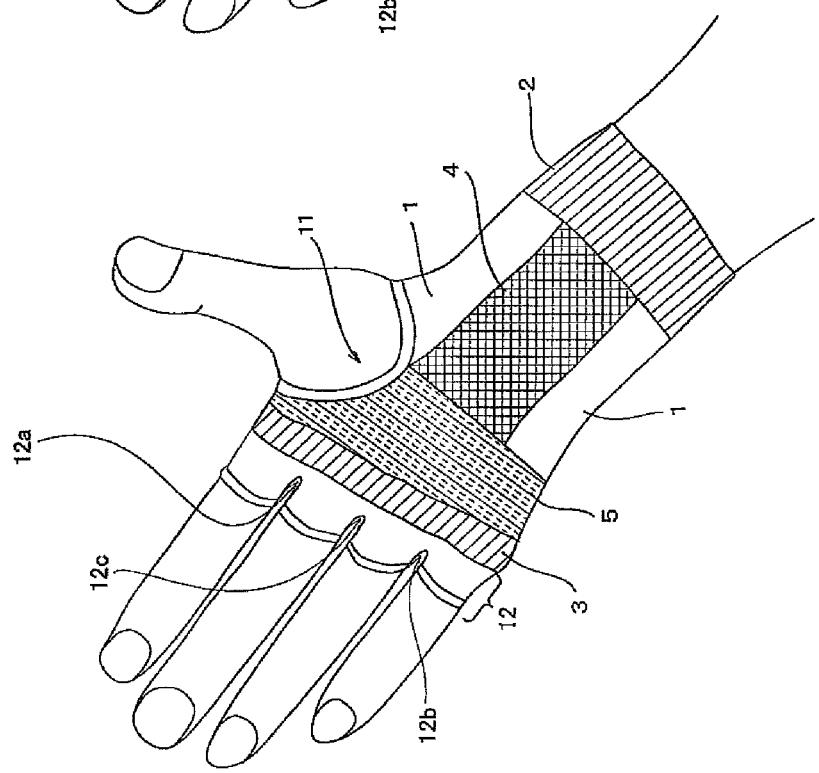
FIG. 10(b) is a perspective view showing a wearing state of the hand joint supporter shown in FIG. 9.

FIG. 8(a) is a front view showing the schematic configuration of a hand joint supporter related to the second embodiment, FIG. 8(b) is a back view of the hand joint supporter shown in FIG. 8(a), FIG. 8(c) is a left side view of the hand joint supporter shown in FIG. 8(a), FIG. 8(d) is a right side view of the hand joint supporter shown in FIG. 8(a), and FIG. 8(e) is a plan view and bottom view of the hand joint supporter shown in FIG. 8(a). FIG. 9(a) is a front view showing the schematic configuration of another hand joint supporter related to the second embodiment, FIG. 9(b) is a back view of the hand joint supporter shown in FIG. 9(a), FIG. 9(c) is a left side view of the hand joint supporter shown in FIG. 9(a), FIG. 9(d) is a right side view of the hand joint supporter shown in FIG. 9(a), and FIG. 9(e) is a plan view and bottom view of the hand joint supporter shown in FIG. 9(a). FIG. 10(a) is a perspective view showing a wearing state of the hand joint supporter shown in FIG. 8, and FIG. 10(b) is a perspective view showing a wearing state of the hand joint supporter shown in FIG. 9. In FIGS. 8 to 10, the same symbol as that in FIGS. 1 and 2 denotes the same or equivalent section, and explanation thereof is omitted.

In each drawing described above, the hand joint supporter 10 related to this embodiment is configured to have, in addition to the configuration in the first embodiment, an anchor reinforcing section 12 which is made of a second tubular knitted fabric that is knitted by circular knitting continuously from the second anchor section 3 of the tubular knitted fabric and which spans between the palm and the back of the hand of a wearer in the webbing between the index finger and the middle finger of the wearer, the webbing between the middle finger and the ring finger, and/or the webbing between the ring finger and the little finger, thereby being engaged with the webbing of the wearer. In addition, in the anchor reinforcing section 12, for example, a mesh stitch knitted fabric which stretches well is used as the second tubular knitted fabric, whereby a strong pressing force is not imparted to the webbing between the index finger and the middle finger of the wearer, the webbing between the middle finger and the ring finger, and/or the webbing between the ring finger and the little finger, so that a feeling of discomfort is not induced in the wearer.

It is conceivable that the anchor reinforcing section 12 related to this embodiment has, for example, two engagement portions (a first engagement portion 12a and a second engagement portion 12b) which are engaged with the webbing between the index finger and the middle finger of a wearer and the webbing between the ring finger and the little finger, as shown in FIGS. 8 and 10(a), or three engagement portions (a first engagement portion 12a, a third engagement portion 12c, and a second engagement portion 12b) which are engaged with the webbing between the index finger and the middle finger of a wearer, the webbing between the middle finger and the ring finger, and the webbing between the ring finger and the little finger, as shown in FIGS. 9 and 10(b).

In particular, since compared to the hand joint supporter 10 shown in FIGS. 8 and 10(a), the hand joint supporter 10 shown in FIGS. 9 and 10(b) covers each finger up to the vicinity of the proximal interphalangeal joints of the index finger, the middle finger, the ring finger, and the little finger of a wearer and the number of engagements of the engagement portions of the anchor reinforcing section 12 with the webbings of a wearer is large, so that the contact area with the fingers of the wearer is large, it is possible to stably support the hand joints of the wearer.

In this manner, the hand joint supporter 10 related to this embodiment more reliably supports the hand joints of a wearer by hooking the engagement portions of the anchor reinforcing section 12 on a single or a plurality of webbings, so that the burden on the hand joints is reduced, whereby an inflammation of the tendons of the hand can be prevented.

In addition, the second embodiment is different from the first embodiment only in that the anchor reinforcing section 12 having a single or a plurality of engagement portions is newly disposed at the second anchor section 3 of the hand joint supporter 10, and except the above-described operation and effects by the anchor reinforcing section 12, the same operation and effects as those of the first embodiment are obtained.

REFERENCE SIGNS LIST

1: base fabric section
2: first anchor section
3: second anchor section
4: supporting section
5: buffer section
10: hand joint supporter
10a: upper end
10b: lower end
11: hole anchor section
12: anchor reinforcing section
102: second metacarpal bone
103: third metacarpal bone
104: fourth metacarpal bone
105: fifth metacarpal bone
110: metacarpophalangeal joint
120: carpometacarpal joint
130: radiocarpal joint

The invention claimed is:

1. A hand joint supporter comprising a tubular knitted fabric that is knitted by circular knitting, and is adapted to come into close contact with the body surface of a wearer, thereby assisting hand joints, the hand joint supporter comprising:

a first anchor section which is arranged to go around one end of the tubular knitted fabric and adapted to make the tubular knitted fabric tighten on a forearm of the wearer;

a second anchor section which is arranged to go around another end of the tubular knitted fabric, is adapted to surround portions corresponding to a second metacarpal bone, a third metacarpal bone, a fourth metacarpal bone, and a fifth metacarpal bone in a vicinity of the metacarpophalangeal joints of the wearer, and adapted to make the tubular knitted fabric tighten on a palm and a back of the hand of the wearer;

a hole anchor section comprising an approximately circular through-hole in a vicinity of the second anchor section in the tubular knitted fabric to insert a thumb of the hand of the wearer therethrough;

a supporting section which is arranged to extend in a length direction of the tubular knitted fabric and adapted to extend over portions of the tubular knitted fabric corresponding to the carpometacarpal joints of the wearer on the front face and/or back face side of the tubular knitted fabric and is connected to the first anchor section and the hole anchor section, thereby supporting the hand joints of the wearer;

a base fabric section which is arranged to surround portions corresponding to the hand joints of the wearer along with the supporting section and adapted to support the hand joints of the wearer along with the supporting section; and a buffer section which is a knitted fabric surrounded by the second anchor section, the hole anchor section, the supporting section, and the base fabric section in the tubular knitted fabric and provides flexibility between the second anchor section and the supporting section;

wherein a stretch resistance of the first anchor section in a circumferential direction of the tubular knitted fabric is larger than a stretch resistance of the base fabric section in the circumferential direction of the tubular knitted fabric; and a stretch resistance of the supporting section in the length direction of the tubular knitted fabric is larger than the stretch resistance of the base fabric section in the length direction of the tubular knitted fabric.

2. The hand joint supporter according to claim 1, wherein a stretch resistance of the base fabric section in the length direction of the tubular knitted fabric is larger than a stretch resistance of the first anchor section in the length direction of the tubular knitted fabric, the stretch resistance of the first anchor section in the length direction of the tubular knitted fabric is larger than a stretch resistance of the second anchor section in the length direction of the tubular knitted fabric, and the stretch resistance of the second anchor section in the length direction of the tubular knitted fabric is larger than a stretch resistance of the buffer section in the length direction of the tubular knitted fabric.

3. The hand joint supporter according to claim 2, wherein stretch resistances of the base fabric section and the supporting section in a circumferential direction of the tubular knitted fabric are larger than the stretch resistance of the second anchor section in the circumferential direction of the tubular knitted fabric, and the stretch resistance of the second anchor section in the circumferential direction of the tubular knitted fabric is larger than a stretch resistance of the buffer section in the circumferential direction of the tubular knitted fabric.

4. The hand joint supporter according to claim 2, further comprising:

an anchor reinforcing section which is made of a second tubular knitted fabric that is knitted by circular knitting continuously from the second anchor section of the tubular knitted fabric, and is adapted to span between the palm and the back of the hand of the wearer in a webbing between an index finger and a middle finger of the wearer, a webbing between the middle finger and a ring finger, and/or a webbing between the ring finger and a little finger, thereby being engaged with each of said webbings of the wearer.

5. The hand joint supporter according to claim 1, wherein the stretch resistances of the base fabric section and the supporting section in the circumferential direction of the tubular knitted fabric are larger than a stretch resistance of the second anchor section in the circumferential direction of the tubular knitted fabric, and the stretch resistance of the second anchor section in the circumferential direction of the tubular knitted fabric is larger than a stretch resistance of the buffer section in the circumferential direction of the tubular knitted fabric.

6. The hand joint supporter according to claim 5, further comprising:

an anchor reinforcing section which is made of a second tubular knitted fabric that is knitted by circular knitting continuously from the second anchor section of the tubular knitted fabric, and is adapted to span between the palm and the back of the hand of the wearer in a webbing between an index finger and a middle finger of the wearer, a webbing between the middle finger and a ring finger, and/or a webbing between the ring finger and a little finger, thereby being engaged with each of said webbings of the wearer.

7. The hand joint supporter according to claim 1, further comprising:

an anchor reinforcing section which is made of a second tubular knitted fabric that is knitted by circular knitting continuously from the second anchor section of the tubular knitted fabric, and is adapted to span between the palm and the back of the hand of the wearer in a webbing between an index finger and a middle finger of the wearer, a webbing between the middle finger and a ring finger, and/or a webbing between the ring finger and a little finger, thereby being engaged with each of said webbings of the wearer.

8. A hand joint supporter comprising a tubular knitted fabric that is knitted by circular knitting, and is adapted to come into close contact with the body surface of a wearer, thereby assisting hand joints, the hand joint supporter comprising:

a first anchor section which is arranged to go around one end of the tubular knitted fabric and adapted to make the tubular knitted fabric tighten on a forearm of the wearer;

a second anchor section which is arranged to go around another end of the tubular knitted fabric, is adapted to surround portions corresponding to a second metacarpal bone, a third metacarpal bone, a fourth metacarpal bone, and a fifth metacarpal bone in a vicinity of the metacarpophalangeal joints of the wearer, and adapted to make the tubular knitted fabric tighten on a palm and a back of the hand of the wearer;

a hole anchor section comprising an approximately circular through-hole in a vicinity of the second anchor section in the tubular knitted fabric to insert a thumb of the hand of the wearer therethrough;

a supporting section which is arranged to extend in a length direction of the tubular knitted fabric and adapted to extend over portions of the tubular knitted fabric corresponding to the carpometacarpal joints of the wearer on the front face and/or back face side of the tubular knitted fabric and is connected to the first anchor section and the hole anchor section, thereby supporting the hand joints of the wearer;

a base fabric section which is arranged to surround portions corresponding to the hand joints of the wearer along with the supporting section and adapted to support the hand joints of the wearer along with the supporting section; and a buffer section which is a knitted fabric surrounded by the second anchor section, the hole anchor section, the supporting section, and the base fabric section in the tubular knitted fabric and provides flexibility between the second anchor section and the supporting section;

wherein a stretch resistance of the base fabric section in the length direction of the tubular knitted fabric is larger than a stretch resistance of the first anchor section in the length direction of the tubular knitted fabric;

the stretch resistance of the first anchor section in the length direction of the tubular knitted fabric is larger than a stretch resistance of the second anchor section in the length direction of the tubular knitted fabric; and the stretch resistance of the second anchor section in the length direction of the tubular knitted fabric is larger than a stretch resistance of the buffer section in the length direction of the tubular knitted fabric.

9. A hand joint supporter comprising a tubular knitted fabric that is knitted by circular knitting, and is adapted to come into close contact with the body surface of a wearer, thereby assisting hand joints, the hand joint supporter comprising:

a first anchor section which is arranged to go around one end of the tubular knitted fabric and adapted to make the tubular knitted fabric tighten on a forearm of the wearer;

a second anchor section which is arranged to go around another end of the tubular knitted fabric, is adapted to surround portions corresponding to a second metacarpal bone, a third metacarpal bone, a fourth metacarpal bone, and a fifth metacarpal bone in a vicinity of the metacarpophalangeal joints of the wearer, and adapted to make the tubular knitted fabric tighten on a palm and a back of the hand of the wearer;

a hole anchor section comprising an approximately circular through-hole in a vicinity of the second anchor section in the tubular knitted fabric to insert a thumb of the hand of the wearer therethrough;

a supporting section which is arranged to extend in a length direction of the tubular knitted fabric and adapted to extend over portions of the tubular knitted fabric corresponding to the carpometacarpal joints of the wearer on the front face and/or back face side of the tubular knitted fabric and is connected to the first anchor section and the hole anchor section, thereby supporting the hand joints of the wearer;

a base fabric section which is arranged to surround portions corresponding to the hand joints of the wearer along with the supporting section and adapted to support the hand joints of the wearer along with the supporting section; and a buffer section which is a knitted fabric surrounded by the second anchor section, the hole anchor section, the supporting section, and the base fabric section in the tubular knitted fabric and provides flexibility between the second anchor section and the supporting section;

wherein the stretch resistances of the base fabric section and the supporting section in the circumferential direction of the tubular knitted fabric are larger than a stretch resistance of the second anchor section in the circumferential direction of the tubular knitted fabric; and the stretch resistance of the second anchor section in the circumferential direction of the tubular knitted fabric is larger than a stretch resistance of the buffer section in the circumferential direction of the tubular knitted fabric.

* * * * *